US00PP35838P2

(12) United States Plant Patent
Kievit et al.

(10) Patent No.: US PP35,838 P2
(45) Date of Patent: May 28, 2024

(54) ***CENTAUREA* PLANT NAMED 'Balcentsirl'**

(50) Latin Name: *Centaurea ragusina*
Varietal Denomination: Balcentsirl

(71) Applicant: Ball Horticultural Company, West Chicago, IL (US)

(72) Inventors: Christa Kievit, Hem (NL); Karl F. Batschke, Geneva, IL (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 18/371,955

(22) Filed: Sep. 22, 2023

(51) Int. Cl.
*A01H 5/02* (2018.01)
*A01H 6/14* (2018.01)

(52) U.S. Cl.
USPC ..... Plt./263.1
CPC ..... *A01H 6/14* (2018.05)

(58) Field of Classification Search
USPC ..... Plt./263.1
CPC ..... A01H 6/14; A01H 5/02
See application file for complete search history.

*Primary Examiner* — Keith O. Robinson
(74) *Attorney, Agent, or Firm* — Audrey Charles

(57) ABSTRACT

A new and distinct cultivar of *Centaurea* plant named 'Balcentsirl', characterized by bright, yellow-colored inflorescences, light silvery, greyed-green colored foliage, and moderately vigorous, compact-mounded growth habit, is disclosed.

1 Drawing Sheet

Latin name of genus and species of plant claimed: *Centaurea ragusina.*
Variety denomination: 'Balcentsirl'.

BACKGROUND OF THE INVENTION

The present invention relates to a new and distinct cultivar of *Centaurea* plant botanically known as *Centaurea ragusina* and hereinafter referred to by the cultivar name 'Balcentsirl'.

The new cultivar originated in a controlled breeding program in Hem, The Netherlands during September 2016. The objective of the breeding program was the development of *Centaurea* cultivars having good winter hardiness and a mounded growth habit suitable for borders and container plantings.

The new *Centaurea* cultivar is the result of open-pollination. The female (seed) parent of the new cultivar is the proprietary *Centaurea ragusina* breeding selection coded A14, not patented, characterized by its bright, yellow-colored flowers, light silvery, greyed-green colored foliage, and moderately vigorous, mounded growth habit. The male (pollen) parent of the new cultivar is unknown. The new cultivar was discovered and selected as a single flowering plant within the progeny of the above stated open-pollination during August 2017 in a controlled environment in Hem, The Netherlands.

Asexual reproduction of the new cultivar by terminal stem cuttings since August 2017 in Hem, The Netherlands and Elburn, Illinois has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Balcentsirl' as a new and distinct cultivar of *Centaurea* plant:

1. Bright, yellow-colored inflorescences;
2. Light silvery, greyed-green colored foliage; and
3. Moderately vigorous, compact-mounded growth habit.

Plants of the new cultivar differ from plants of the female parent primarily in having a more silvery-colored foliage, and deeper leaf incisions.

Of the many commercially available *Centaurea* cultivars, the most similar in comparison to the new cultivar is the 'Snowy Owl', not patented. However, in comparison, plants of the new cultivar differ from plants of 'Snowy Owl' in at least the following characteristics:

1. Plants of the new cultivar is winter hardy to lower temperatures than plants of the Zone 9 hardy 'Snowy Owl'; and
2. Plants of the new cultivar have more deeply incised leaves than plants of 'Snowy Owl'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Balcentsirl'. The plants were approximately 16-months old. The plants were grown in one-gallon containers in an outdoor nursery in West Chicago, Illinois for approximately four months and then overwintered in a polycarbonate greenhouse in Elburn, Illinois.

DETAILED BOTANICAL DESCRIPTION

Figure 1:
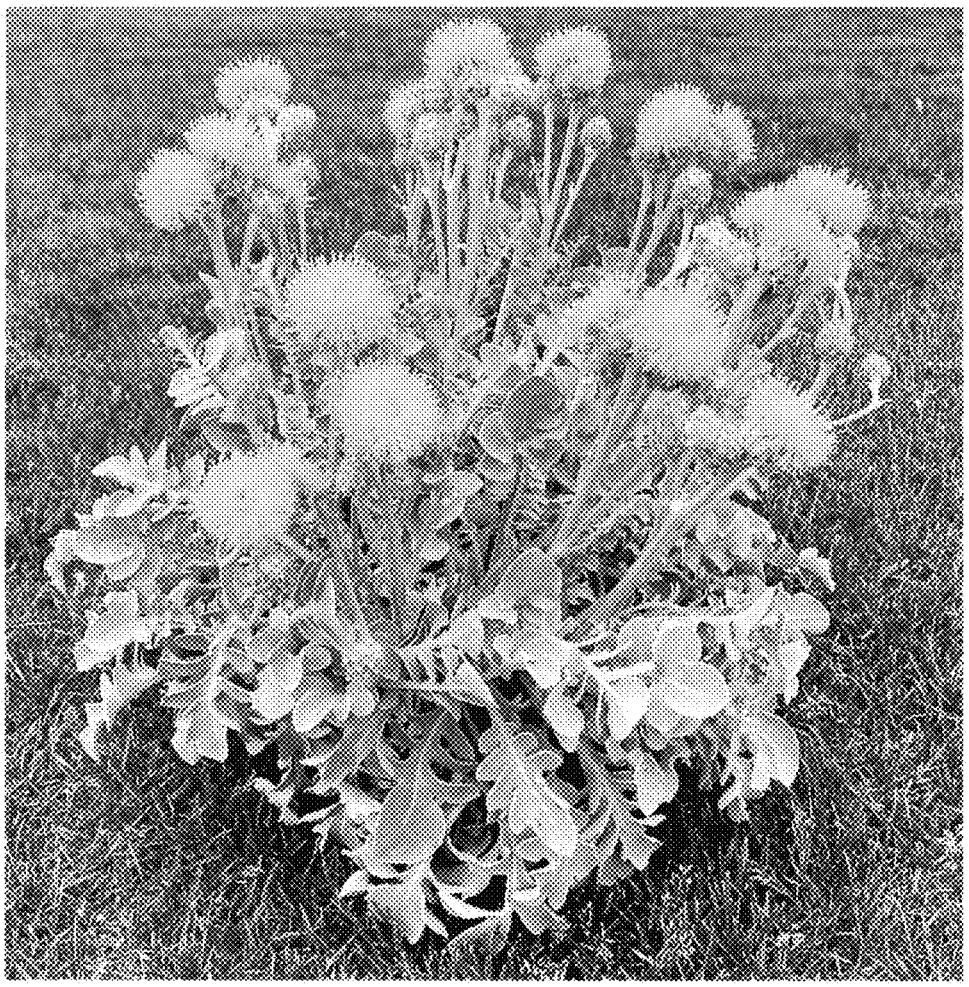
FIG. 1 illustrates a side view of the overall growth and flowering habit of 'Balcentsirl'.
Figure 2:
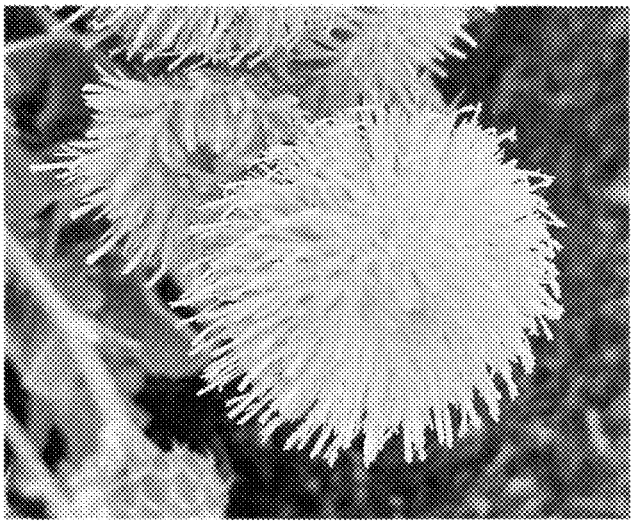
FIG. 2 illustrates a close-up view of an inflorescence of 'Balcentsirl'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used. The color values were determined in May 2023 under natural light conditions in Naperville, Illinois.

The following descriptions and measurements describe approximately 16-month-old plants produced from cuttings from stock plants and grown under conditions comparable to those used in commercial practice. The plants were grown in one-gallon containers in an outdoor nursery in West Chicago, Illinois for approximately four months and then overwintered in a polycarbonate greenhouse in Elburn, Illinois. Overwintering greenhouse temperatures were maintained at approximately 60° F. to 65° F. (15.5° C. to 18.3° C.) during the day and approximately 55° F. to 60° F. (12.7° C. to 15.5° C.) during the night. No supplemental lighting was provided during overwintering. Measurements and numerical values represent averages of typical plants.

Botanical classification: *Centaurea ragusina* 'Balcentsirl'.

Parentage:

*Female parent.*—Proprietary *Centaurea ragusina* breeding selection coded A14, not patented.

*Male parent.*—Unknown.

Propagation:

*Type cutting.*—Terminal stem.

*Time to initiate roots.*—Approximately 6 to 7 days.

*Time to produce a rooted cutting.*—Approximately 5 to 6 weeks.

*Root description.*—Fibrous, medium thickness.

*Rooting habit.*—Freely branching, dense.

Plant description:

*Commercial crop time.*—Approximately 6 to 8 weeks from a rooted cutting to finish in a 15 cm container.

*Growth habit and general appearance.*—Herbaceous perennial, moderately vigorous, mounded growth habit.

*Hardiness.*—USDA zone 6b (−5° F. to 0° F./−20.6° C. to −17.8° C.).

*Size.*—Height from soil level to top of plant plane: Approximately 35.0 cm. Width: Approximately 44.0 cm.

*Branching habit.*—Clump forming, freely branching, pinching improves basal branching. Quantity: 16.

Foliage description:

*General description.*—Quantity of leaves per clump: Approximately 12. Type: Simple. Fragrance: None detected. Arrangement: Basal whorls, alternate on peduncle. Aspect: Petiole is acute angle to stem with leaf extending downward with age.

*Leaves.*—Shape: Pinnatisect. Margin: Entire, wavy. Apex: Apiculate. Base: Attenuate. Venation pattern: Pinnate. Length: Approximately 10.0 cm. Width: Approximately 6.0 cm. Texture of upper and lower surfaces: Densely tomentose. Color of upper surface of young and mature foliage: 137A but appears 190A due to tomentose of NN155D, venation of 190D. Color of lower surface of young and mature foliage: 137A but appears 190B due to tomentose of NN155D, venation of 190D.

*Petiole.*—Length: Approximately 8.0 cm. Width: Approximately 9.0 cm. Texture: Densely tomentose. Color: 146B but appears 190C to 190D due to tomentose of NN155D.

Flowering description:

*Flowering habit.*—'Balcentsirl' is freely flowering under outdoor growing conditions with substantially continuous blooming in spring to early summer.

*Lastingness of individual inflorescence on the plant.*—Approximately 2 weeks.

Inflorescence description:

*General description.*—Type: Composite heads, thistle-like, actinomorphic. Shape: Globular. Aspect: Erect to outwardly facing. Arrangement: Terminal capitulum, positioned above the foliage, 3 to 5 heads per peduncle. Quantity per plant: Approximately 50. Diameter: Approximately 4.3 cm. Depth: Approximately 3.5 cm. Fragrance: Slightly sweet.

*Peduncle.*—Strength: Strong, flexible. Aspect: Erect. Length: Approximately 23.0 cm with branches of 3.0 cm to 13.0 cm. Diameter: Approximately 4.0 mm to 6.0 mm. Texture: Densely tomentose of NN155D. Color: 146B but appears 190D due to tomentose.

*Bud.*—Rate of opening: Generally takes approximately 2 to 3 weeks for bud to progress from first color to fully open inflorescence. Quantity per plant: Approximately 19.

*Bud just before opening.*—Shape: Ovoid. Width: Approximately 2.0 cm. Length: Approximately 2.0 cm. Color: 137A but appears 190D due to tomentose of NN155D, apex of bud papery translucent of N199D.

*Disc florets.*—Quantity per inflorescence: Approximately 170. Arrangement: Head, lower half of florets surrounded by involucre bracts. Shape: Tubular with five lobes approximately 5.0 mm in length and approximately 1.0 mm in width at base; pappus of bristles at base of tube NN155D in color and approximately 4.0 mm in length. Margin: Entire. Apex of lobes: Acute. Base: Fused. Length: Approximately 3.0 mm. Diameter at tube opening with flared lobes: Approximately 5.0 mm. Diameter at base: Approximately 1.0 mm. Texture of outer and inner surfaces: Glabrous. Color of upper or inner surface when first and fully open: 7A to 7B. Color of lower or outer surface when fully open: 7A to 7B, lower half of NN155D.

*Receptacle.*—Shape: Disc. Height: Approximately 5.0 mm. Diameter: Approximately 2.0 cm. Color: NN155B.

*Involucre bracts.*—Quantity per inflorescence Approximately 36. Arrangement: Imbricate, in multiple whorls. Shape: Ovate. Margin: Entire. Apex: Apiculate, spiny. Base: Truncate. Length: Approximately 7.0 mm. Width: Approximately 7.0 mm. Texture of outer surface: Densely tomentose. Texture of inner surface: Glabrous. Color of outer surface: 137A but appears 190D due to tomentose of NN155D, apex papery translucent of N199D. Color of inner surface: 137A.

*Reproductive organs.*—Androecium: Stamen quantity: 5. Stamen length: Approximately 1.1 cm. Filament length: Approximately 4.0 mm. Filament color: 7B. Anther shape: Oblong, connate around style, basifixed. Anther length: Approximately 7.0 mm. Anther color: 8C. Pollen amount: Moderate. Pollen color: 8C. Gynoecium: Pistil quantity: 1 per floret. Pistil length: Approximately 3.0 cm. Stigma shape: 2-branched. Stigma length: Approximately 1.0 mm. Stigma color: 7B. Style length: Approximately 2.6 cm. Style color: 7B transitioning to NN155D for lower half. Ovary length: Approximately 3.0 mm. Ovary color: NN155D.

Seed and fruit production: Neither seed nor fruit production has been observed.

Disease and pest resistance: Resistance to pathogens and pests common to *Centaurea* has not been observed.

What is claimed is:

1. A new and distinct cultivar of *Centaurea* plant named 'Balcentsirl', substantially as herein illustrated and described.

* * * * *